(12) United States Patent
Gutman et al.

(10) Patent No.: US 7,312,345 B2
(45) Date of Patent: Dec. 25, 2007

(54) PROCESS FOR THE PREPARATION OF DRONEDARONE

(75) Inventors: Arie Gutman, Haifa (IL); Gennadi Nisnevich, Haifa (IL); Lev Yudovitch, Haifa (IL)

(73) Assignee: ISP Investments Inc., Wilmington, DE (US)

( * ) Notice: Subject to any disclaimer, the term of this patent is extended or adjusted under 35 U.S.C. 154(b) by 440 days.

(21) Appl. No.: 10/494,960

(22) PCT Filed: Nov. 6, 2002

(86) PCT No.: PCT/IL02/00881

§ 371 (c)(1),
(2), (4) Date: Oct. 20, 2004

(87) PCT Pub. No.: WO03/040120

PCT Pub. Date: May 15, 2003

(65) Prior Publication Data

US 2005/0049302 A1    Mar. 3, 2005

(30) Foreign Application Priority Data

Nov. 8, 2001   (IL) .................................. 146389

(51) Int. Cl.
*C07D 307/81*  (2006.01)
*C07D 307/83*  (2006.01)
*C07C 233/25*  (2006.01)
*C07C 271/28*  (2006.01)
*C07C 271/58*  (2006.01)

(52) U.S. Cl. ............... 549/466; 549/468; 549/471; 560/29; 564/219

(58) Field of Classification Search ............... 549/466, 549/468, 471; 560/29, 219
See application file for complete search history.

(56) References Cited

U.S. PATENT DOCUMENTS 3,956,385 A  *  5/1976  Suda et al. .................... 564/86
5,223,510 A     6/1993  Gubin et al.
5,990,315 A     11/1999 Dumas

FOREIGN PATENT DOCUMENTS

| WO | WO 97/17346 A1 | 5/1997 |
| WO | WO 01/28974 A2 | 4/2001 |
| WO | WO 01/29019 A1 | 4/2001 |

OTHER PUBLICATIONS

Horton, H. R. et al "Reactions with Reactive Alkyl Halides" Methods in Enzymology, vol. 11 (1967) pp. 556-565.
Raval, A. A. et al "Studies in Chalcones and Related Compounds Derived from 2-Hydroxy-5-acetaminoacetophenone:Part I. Synthesis of 2-Hydroxy-5'-acetaminochalcones and 6-Aminoflavones" J. Org. Chem., 21, (Dec. 1956) pp. 1408-1411.

* cited by examiner

*Primary Examiner*—Bernard Dentz
(74) *Attorney, Agent, or Firm*—Browdy and Neimark, PLLC

(57) ABSTRACT

The present invention provides, according to an aspect thereof, a novel process for the preparation of dronedarone [1] and pharmaceutically acceptable salts thereof. According to a preferred embodiment, the process comprises N-acetylating of p-anisidine or p-phenetidine with acetic anhydride, reacting of the obtained N-(4-alkoxyphenyl)acetamide with 2-bromohexanoyl chloride or bromide in the presence of aluminum chloride or bromide to obtain N-[3-(2-bromohexanoyl)-4-hydroxyphenyl]acetamide [6a], converting the compound [6a] into 2-butyl-5-benzofuranamine hydrochloride [12a] and subsequently converting [12a] into [1] or pharmaceutically acceptable salts thereof. In accordance with another aspect of this invention, there are provided novel intermediates, inter alia the novel compounds [6a] and [12a]. The novel intermediates of the present invention are stable, solid compounds, obtainable in high yields, which can be easily purified by crystallization and stored for long periods of time.

15 Claims, No Drawings

PROCESS FOR THE PREPARATION OF DRONEDARONE

FIELD OF THE INVENTION

The present invention relates to a novel process for the preparation of dronedarone and pharmaceutically acceptable salts thereof, to novel intermediates used in this process and their preparation.

PRIOR ART

The following references are considered to be pertinent for the purpose of understanding the background of the present invention:
U.S. Pat. No. 5,223,510;
H. R. Horton and D. E. Koshland, J. Methods in Enzymology, 1967, v. 11, 556;
WO 01/28974 A2;
WO 01/29019 A1; and
U.S. Pat. No. 5,990,315.

BACKGROUND OF THE INVENTION

Dronedarone, SR 33589, N-[2-Butyl-3-[4-[3-(dibutylamino)propoxy]benzoyl]-5-benzofuranyl]methanesulfonamide, having the formula [1]:

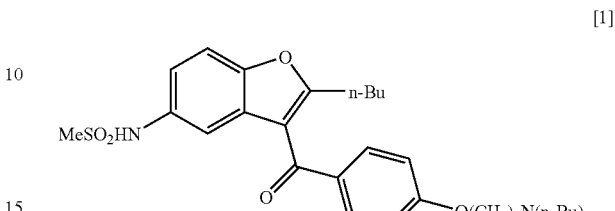

is a drug for the treatment of arrhythmia (U.S. Pat. No. 5,223,510).

A prior art method for preparing dronedarone [1], disclosed in U.S. Pat. No. 5,223,510, starts from 2-butyl-5-nitrobenzofuran according to the following Scheme 1:

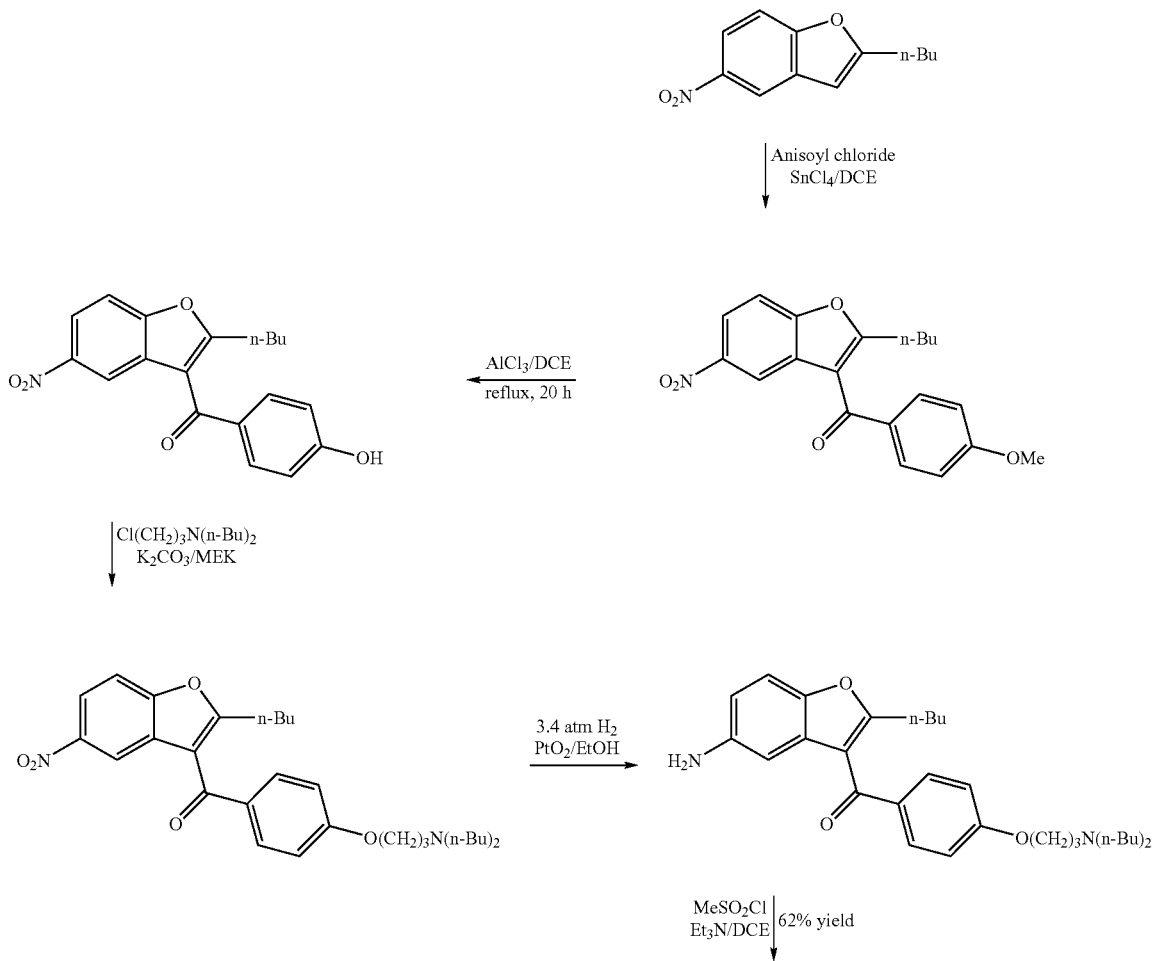

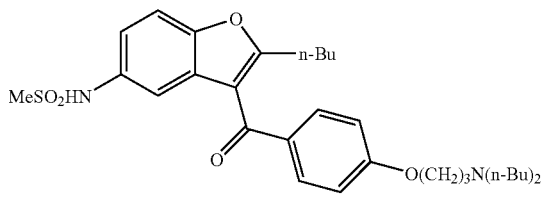

[1]

The starting material 2-butyl-5-nitrobenzofuran is prepared by multi-stage processes, as showed in Scheme 2 (U.S. Pat. No. 5,223,510, H. R. Horton and D. E. Koshland, J. Methods in Enzymology, 1967, v. 11, 556) and Scheme 3 (WO 01/28974 A2 and WO 01/29019 A1):

Scheme 2

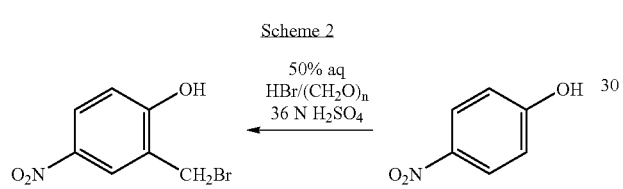

-continued

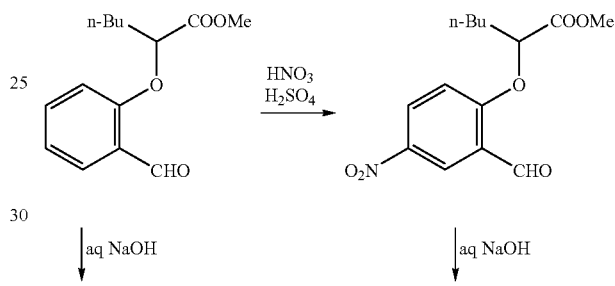

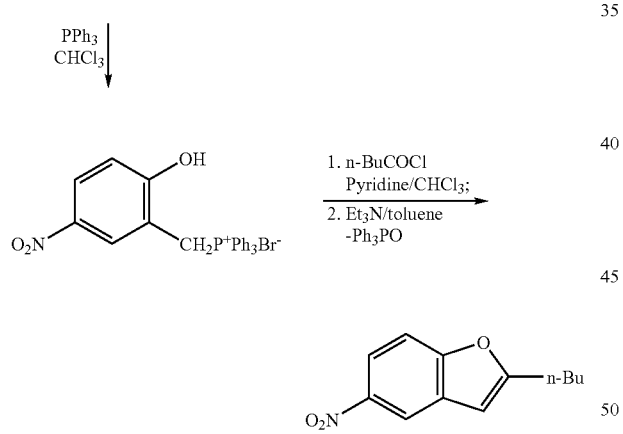

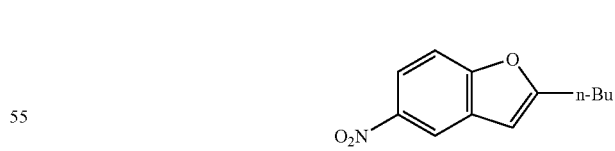

It is known that catalytic reduction of 2-butyl-5-nitrobenzofuran (3.4 atm $H_2/PtO_2/EtOH$) gives 2-butyl-5-benzofuranamine free base, which reacts with methanesulfonyl chloride in the presence of triethylamine as acid scavenger and carbon tetrachloride as a solvent to give N-(2-butyl-5-benzofuranyl)-N-(methylsulfonyl)methanesulfonamide [14a] instead of N-(2-butyl-5-benzofuranyl)methanesulfonamide [14] (U.S. Pat. No. 5,223,510, Scheme 4):

Scheme 3

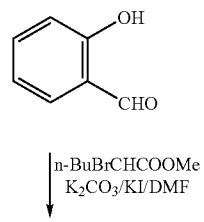

Scheme 4

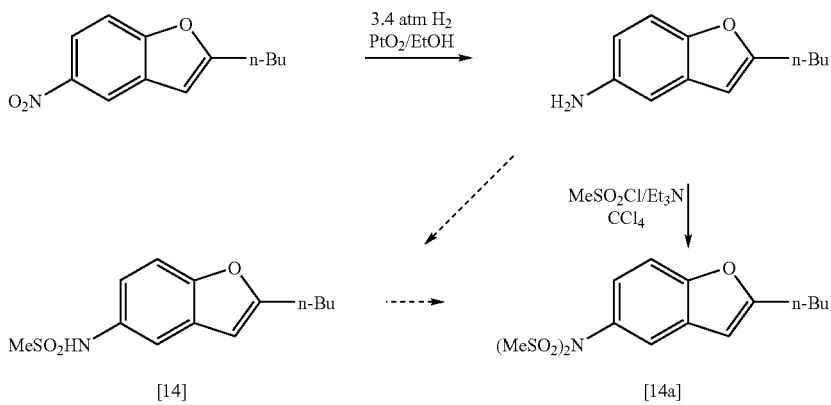

Compound [14a] may be converted back to [14] but this necessitates the use of larger amounts of methanesulfonyl chloride and of acid scavenger, thus causing increased costs. It also has to be noted that 2-butyl-5-benzofuranamine free base is an unstable compound and can not be stored for long periods of time.

SUMMARY OF INVENTION

It is an object of the present invention to provide a novel process for the preparation of dronedarone and its pharmaceutically acceptable salts, which is free of the above-mentioned disadvantages, starting with commercially available materials and using simple reagents and low cost solvents, to afford high overall yield of the product.

The above object is achieved in accordance with the present invention which, in one aspect thereof, provides a process for preparing dronedarone [1] and pharmaceutically acceptable salts thereof, starting with commercially available materials such as p-anisidine or p-phenetidine. Thus, the process of the invention comprises the steps of:

(a) reacting a compound of formula [3] with 2-bromohexanoyl chloride or bromide in the presence of aluminum chloride or bromide to obtain a compound of formula [6]:

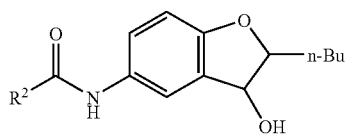
[3]

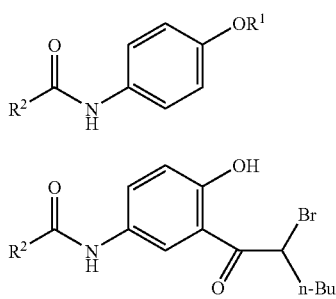
[6]

wherein $R^1$ is methyl or ethyl; $R^2$ is selected from alkyl, aryl, aralkyl, alkoxy, aryloxy, and aralkoxy;

(b) converting the compound [6] obtained in step (a) above into the compound of formula [9]:

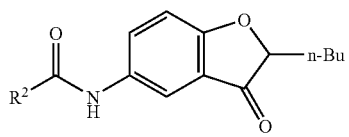
[9]

without isolation of the intermediate compounds [7] or [8]:

[7]

[8]

wherein $R^2$ is as defined above;

(c) dehydrating and N-deprotecting the compound of formula [9] obtained in step (b) above in aqueous solution of $HX^4$, wherein $HX^4$ is selected from hydrogen chloride, hydrogen bromide, sulfuric acid, methanesulfonic acid and p-toluenesulfonic acid, to obtain the solid salt of 2-butyl-5-benzofuranamine [12]

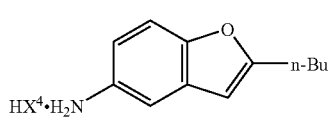
[12]

without isolation of the intermediate compounds [10] or [1]:

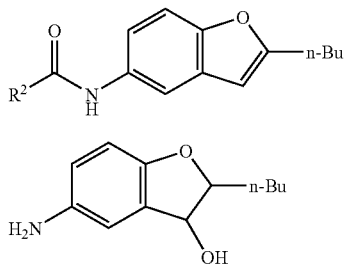
[10]

[11]

wherein $R^2$ is as defined above;

(d) optionally, preparing 2-butyl-5-benzofuranamine free base from the acid addition salt of 2-butyl-5-benzofuranamine [12] obtained in step (c) above;

(e) reacting the 2-butyl-5-benzofuranamine free base obtained in step (d) above or the acid addition salt of 2-butyl-5-benzofuranamine [12] obtained in step (c) with an agent selected from methanesulfonic anhydride and methanesulfonyl chloride or fluoride to obtain N-(2-butyl-5-benzofuranyl)methanesulfonamide [14]

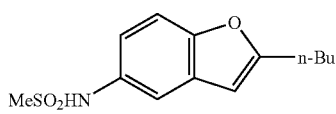
[14]

(f) Friedel-Crafts acylating the compound [14] obtained in step (e) above with 4-(3-dibutylaminopropoxy)benzoyl chloride hydrochloride [15]

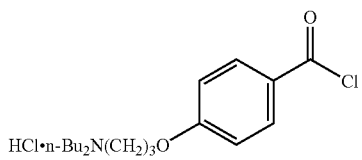
[15]

to obtain dronedarone [1] or a pharmaceutically acceptable salt thereof.

According to a preferred embodiment, the present invention provides a process for preparing dronedarone [1] and pharmaceutically acceptable salts thereof, which comprises N-acetylating of p-anisidine or p-phenetidine with acetic anhydride, reacting of the obtained N-(4-alkoxyphenyl)acetamide with 2-bromohexanoyl chloride or bromide in the presence of aluminum chloride or bromide to obtain N-[3-(2-bromohexanoyl)-4-hydroxyphenyl]acetamide [6a], converting the compound [6a] into 2-butyl-5-benzofuranamine hydrochloride [12a] and subsequently converting [12a] into [1] or pharmaceutically acceptable salts thereof.

The intermediates [6], [9], [10] and the acid addition salts of 2-butyl-5-benzofuranamine [12] are new compounds and constitute another aspect of the present invention. The novel intermediates of the present invention are obtained in stable, solid form. In addition, they are obtained in high yields, may be easily purified by crystallization and stored for long periods of time.

DETAILED DESCRIPTION OF THE INVENTION

Compounds of formula [3] may be prepared by methods known in the art, by reacting p-anisidine or p-phenetidine with compounds of formula [2]:

$$R^2COX^1 \quad [2]$$

wherein $R^2$ is selected from alkyl, aryl, aralkyl, alkoxy, aryloxy and aralkoxy and $X^1$ is $R^2COO-$, chloride or bromine.

The reaction of [3] with 2-bromohexanoyl chloride or bromide is carried out under Friedel-Crafts reaction conditions using more than one equivalent of aluminum chloride or bromide as Lewis acid catalyst and O-deprotecting reagent. Preferably, from 2 to 4 moles of aluminum chloride or bromide are used with 1 mole of compound [3]. Preferably, the reaction is carried out in the presence of nitroalkane or nitroarene—chelating agents increasing the solubility of aluminum compounds and improving the yields of the reaction. Preparation of compound [6] from p-anisidine or p-phenetidine is depicted in Scheme 5:

Scheme 5

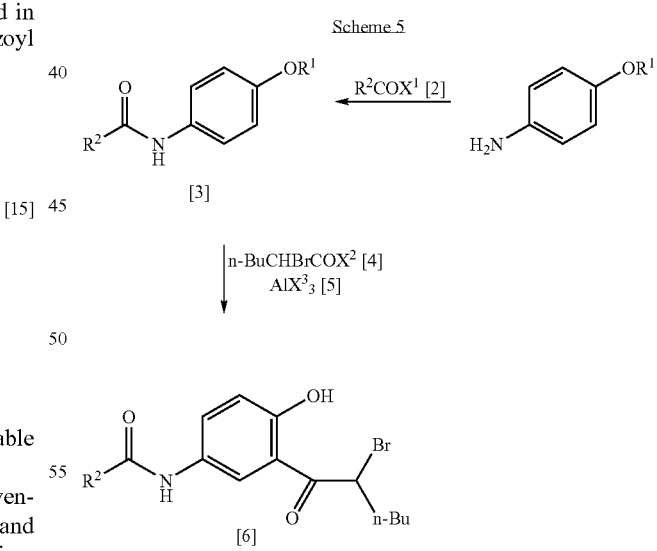

wherein $R^1$ is methyl or ethyl; $R^2$ is selected from alkyl, aryl, aralkyl, alkoxy, aryloxy or aralkoxy; $X^1$ is $R^2COO-$, chlorine or bromine; $X^2$ is chlorine or bromine and $X^{3'}$ is chlorine or bromine.

Preferably, compound [6] is converted to compound [12] without isolating the intermediate compounds [7-11] using the "one pot" process depicted in Scheme 6:

Scheme 6

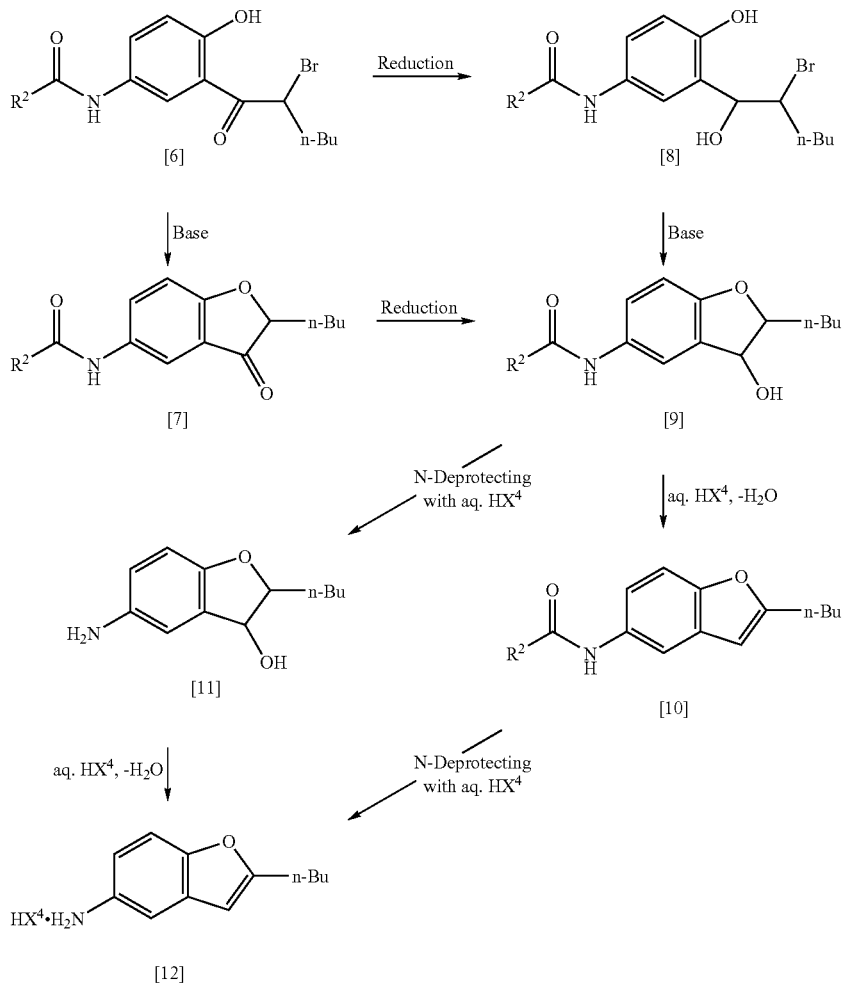

wherein $R^2$ is selected from alkyl, aryl, aralkyl, alkoxy, aryloxy and aralkoxy and $HX^4$ is selected from hydrogen chloride, hydrogen bromide, sulfuric acid, methanesulfonic acid or p-toluenesulfonic acid.

It should be noted that each step of the above process may be successfully carried out as individual reaction steps and all the compounds [8-11], except for the unstable compound [7], may be isolated and used as precursors for the preparation of compound [12]. Compounds [6], [9], [10] and [12] are stable, solid compounds which can be easily purified by crystallization and stored for long periods of time.

Preferably, the reductions according to Scheme 6 are carried out in the presence of sodium borohydride as reductive agent. Preferably, the base according to Scheme 6 is a metal bicarbonate or acetate. Preferably $R^2$ is methyl and $R^2COX^1$ in this case is acetic anhydride. $HX^4$ is preferably HCl.

Preferably, the process for the preparation of dronedarone [1] or pharmaceutically acceptable salts thereof according to the present invention includes the steps of:

(a) N-acetylating p-anisidine or p-phenetidine with acetic anhydride and reacting the obtained N-(4-alkoxyphenyl) acetamide with 2-bromohexanoyl chloride or bromide in the presence of aluminum chloride or bromide to form N-[3-(2-bromohexanoyl)-4-hydroxyphenyl]acetamide [6a];

(b) converting the compound [6a] obtained in step (a) above into 2-butyl-5-benzofuranamine hydrochloride [12a] by "one-pot" procedure;

(c) optionally, preparing 2-butyl-5-benzofuranamine free base from 2-butyl-5-benzofuranamine hydrochloride [12a] obtained in step (b) above;

(d) reacting the 2-butyl-5-benzofuranamine free base obtained in step (c) above or 2-butyl-5-benzofuranamine hydrochloride [12a] obtained in step (b) with methanesulfonyl chloride without addition any other acid scavenger to obtain N-(2-butyl-5-benzofuranyl)methanesulfonamide [14]:

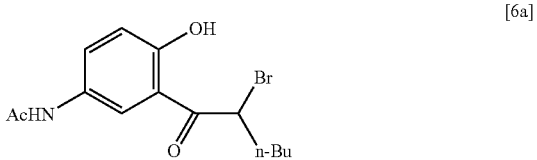

[6a]

-continued
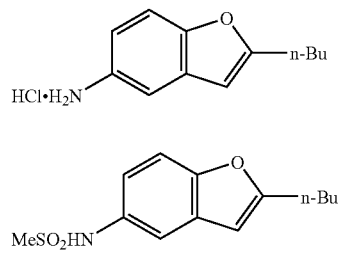
[12a]
(e) Friedel-Crafts acylating of N-(2-butyl-5-benzofuranyl) methanesulfonamide [14] obtained in step (d) above with 4-(3-dibutylaminopropoxy)benzoyl chloride hydrochloride [15] to obtain dronedarone [1] or a pharmaceutically acceptable salt thereof:
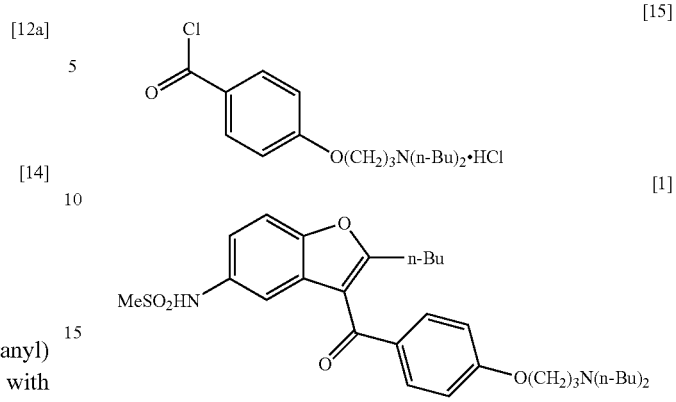
The above process is showed in the following Schemes 7 and 8.
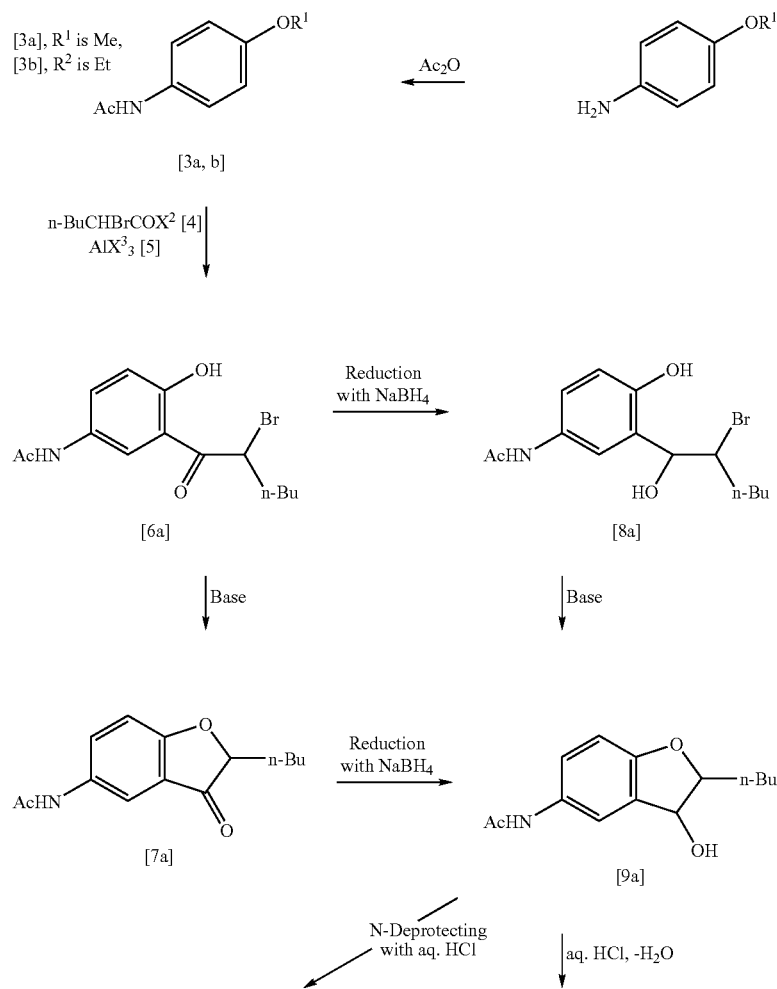
Scheme 7

-continued

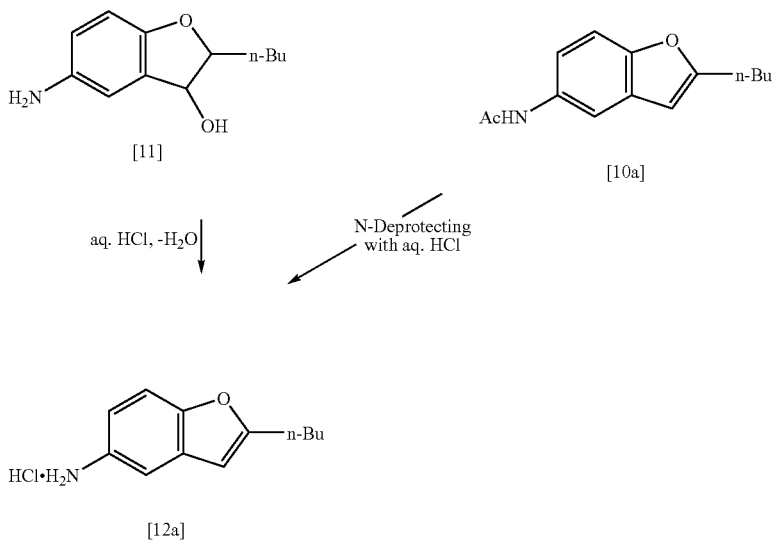

wherein R¹ is methyl or ethyl and X² and X³ are independently selected from chlorine and bromine.

The compound [12a] may be converted into dronedarone [1] by the method depicted in Scheme 8 below:

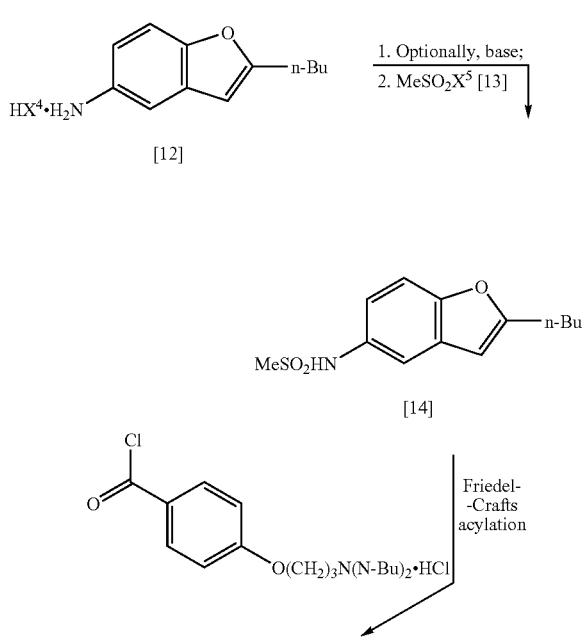

wherein $X^5$ is selected from chlorine, fluorine and methanesulfonyl group. $X^5$ is preferably chlorine.

In the preparation of N-(2-butyl-5-benzofuranyl)methanesulfonamide [14] it is difficult to drive the conversion of 2-butyl-5-benzofuranamine to completion in the presence of a base without the formation of a substantial quantity of N-(2-butyl-5-benzofuranyl)-N-(methylsulfonyl)methanesulfonamide [14a]. In order to optimize the conversion of 2-butyl-5-benzofuranamine to the desired compound [14] it is necessary to stop the reaction when only partial conversion of the aryl amine has been achieved. This leads to reduced yields which can be compensated for by additional processing to recover 2-butyl-5-benzofuranamine. Alternatively, the reaction can be driven to completion in the presence of a base and the co-product [14a] converted back to the secondary sulfonamide [14]. The reaction of 2-butyl-5-benzofuranamine or its salt with methanesulfonyl chloride can be carried out according to a procedure described in U.S. Pat. No. 5,990,315.

Preferably the catalyst in the Friedel-Crafts acylation of N-(2-butyl-5-benzofuranyl)methanesulfonamide [14] is a Lewis acid. Preferably the Lewis acid is tin (IV) chloride.

4-(3-Dibutylaminopropoxy)benzoyl chloride hydrochloride [15] is obtained from compound 1161 according to Scheme 9:

Scheme 9

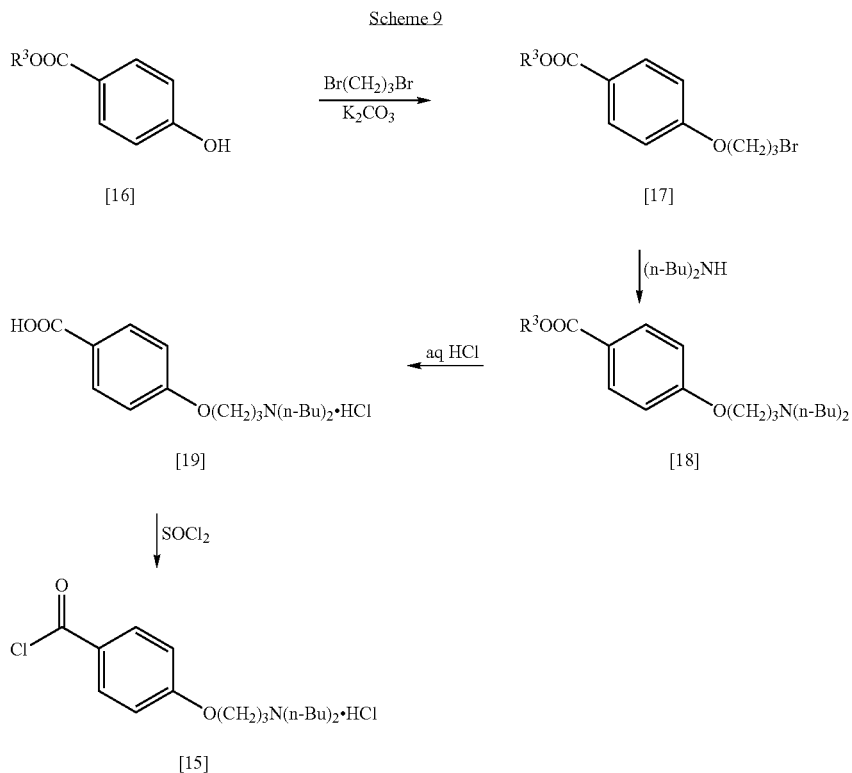

$R^3$ is an alkyl group, and preferably methyl.

The compound [19] is preferably prepared by a "one-pot" procedure from compound [16] without isolating the intermediate compounds [17] and [18].

This invention will be better understood from the Examples that follow. However, the examples illustrate, but do not limit, the invention. Those skilled in the art will readily appreciate that the specific methods and results discussed are merely illustrative of the invention as described and claimed in the claims that follow thereafter.

EXAMPLES

Example 1

Scheme 10

N-(4-Methoxyphenyl)acetamide [3a]

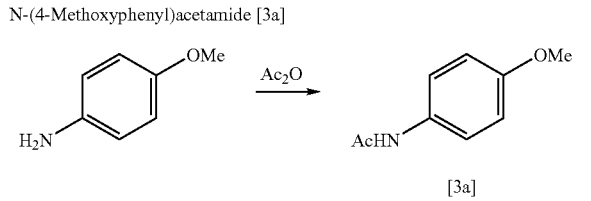

Acetic anhydride (10.21 g, 9.4 mL, 100 mmol) was added dropwise over 1 hour to a stirred solution of p-anisidine (12.32 g, 100 mmol) in dichloromethane (40 mL) at 25-30° C. The mixture was stirred for an additional 1 hour at the same temperature. Hexane (120 mL) was added dropwise to the mixture at 25-30° C. The obtained suspension was stirred for 1 hour at the same temperature. The precipitated crystals were separated by filtration and dried under reduced pressure to give 15.31 g (92.7%) of N-(4-methoxyphenyl)acetamide [3a] as off-white crystals.

$^1$H NMR (CDCl$_3$): 7.84 (bs, 1H), 7.35 (m, 2H), 6.79 (m, 2H), 3.74 (s, 3H), 2.08 (s, 3H).

Example 2

Scheme 11

N[3-(2-Bromohexanoyl)-4-hydroxyphenyl]acetamide [6a]

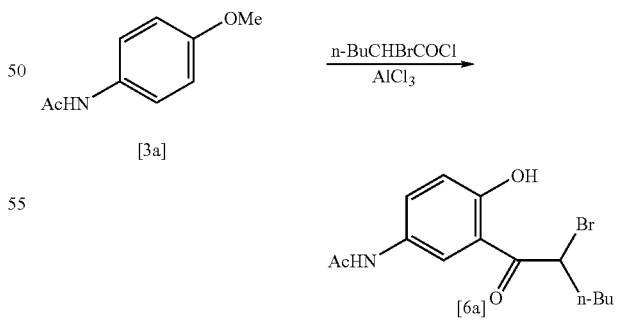

Aluminium chloride (20.00 g, 150 mmol) was carefully added to a stirred solution of N-(4-methoxyphenyl)acetamide [3a] (8.26 g, 50.0 mmol) in dichloromethane (30 mL) at 0-5° C. (ice/water bath). Nitromethane (8.2 mL, 150 mmol) was added to the mixture in one portion. A solution of 2-bromohexanoyl chloride (12.81 g, 60.0 mmol) in dichloromethane (20 mL) was added dropwise to the stirred mixture at room temperature. The obtained mixture was stirred for 4 hours at the same temperature. Aluminum chloride (6.67 g, 50.0 mmol) was added in one portion to the stirred mixture at room temperature. The mixture was stirred overnight at the same temperature. The mixture was carefully poured into ice/water mixture. The mixture was extracted with ethyl acetate (150 mL then 2×50 mL). The combined organic layers were washed with brine (50 mL), dried over sodium sulfate, filtered and evaporated under reduced pressure at 50° C. (water bath). The residue (21.20 g) was stirred with hexane (150 mL) for 1 hour at room temperature. The precipitated solids were filtered off, washed on the filter with hexane and dried at 50° C. (water bath) to the constant weight to give 15.03 g (91.6%) of N-[3-(2-bromohexanoyl)-4-hydroxyphenyl]acetamide [6a] as yellow crystals with mp 137-138° C. (toluene).

$^1$H NMR (CDCl$_3$): 11.79 (s, 1H), 8.16 (d, J=2.2 Hz, 1H), 7.39 (dd, J=8.6 and 2.2 Hz, 1H), 7.38 (bs, 1H), 6.95 (d, J=8.6 Hz, 1H), 5.11 (t, J=7.0 Hz, 1H), 2.16 (s, 3H), 2.11 (m, 2H), 1.36 (m, 4H), 0.90 (t, J=7.2 Hz, 3H).

Example 3

Scheme 12

2-Butyl-5-benzofuranamine hydrochloride [12a]

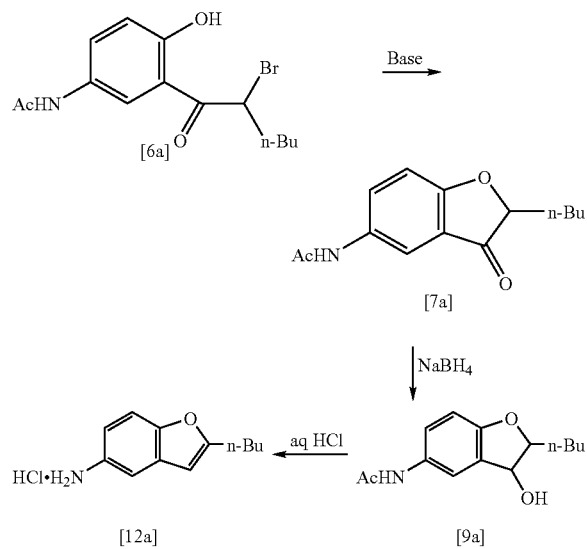

Sodium bicarbonate (3.36 g, 40.0 mmol) was added in several portions to a stirred boiling mixture of N-[3-(2-bromohexanoyl)-4-hydroxyphenyl]acetamide [6a] (13.13 g, 40.0 mmol) and methanol (30 mL). The mixture was stirred under reflux conditions for 2 hour. Sodium borohydride (1.51 g, 40.0 mmol) was added in several portions to the mixture at 0-5° C. (ice/water bath). The mixture was stirred for 30 min at the same temperature and 15% hydrochloric acid (100 mL) was added. The solution was stirred for 4 hours under reflux conditions and for 1 hour at 0-5° C. (ice/water bath). The precipitated crystals were filtered off, washed on the filter with water (20 mL) and ethyl acetate (20 mL) and dried to give 7.62 g (84.5% yield from 3 steps) of 2-butyl-5-benzofuranamine hydrochloride [12a] as off-white crystals with mp 190-193° C. (dec.).

$^1$H NMR (CDCl$_3$): 7.52 (s, 1H), 7.18 (s, 2H), 6.19 (s, 1H), 2.67 (t, J=7.2 Hz, 2H), 1.65 (m, 2H), 1.39 (m, 2H), 0.92 (t, J=7.2 Hz, 3H).

Example 4

Scheme 13

N-(2-Butyl-3-hydroxy-2,3-dihydro-5-benzofuranyl)acetamide [9a]

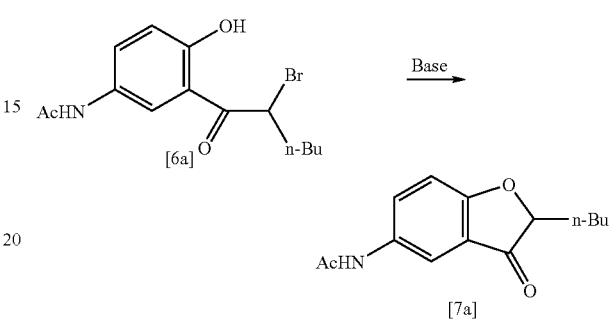

A mixture of N-[3-(2-bromohexanoyl)-4-hydroxyphenyl]acetamide [6a] (3.28 g, 10.0 mmol), sodium bicarbonate (0.84 g, 10.0 mmol) and methanol (30 mL) was stirred under reflux conditions for 2 hours. Sodium borohydride (0.76 g, 20.0 mmol) was added in several portions to the mixture at 0-5° C. (ice/water bath). The mixture was stirred for 1 hour at the same temperature. Methanol (20 mL) was evaporated from the mixture and water (100 mL) was added to the residue. The obtained mixture was stirred for 1 hour at 0-5° C. (ice/water bath). The precipitated crystals were filtered and dried under reduced pressure at 50-60° C. to give 2.01 g (80.6% yield from 2 steps) of N-(2-butyl-3-hydroxy-2,3-dihydro-5-benzofuranyl)acetamide [9a] as off-white crystals with mp 134-137° C.

$^1$H NMR (CDCl$_3$): 7.59 (bs, 1H), 7.48 (m, 1H), 7.13 (m, 1H), 6.69 (m, 1H), 4.89 (dd, J=13.3 and 5.5 Hz, 1H), 4.40 (m, 1H), 2.07 (s, 3H), 1.81 (m, 2H), 1.46 (m, 5H), 0.93 (t, J=7.0 Hz, 3H).

Example 5

Scheme 14

N-(2-Butyl-3-benzofuranyl)acetamide [10a]

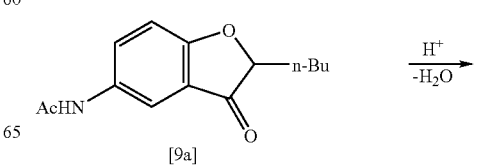

-continued

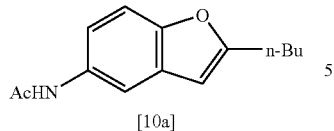
[10a]

A mixture of N-(2-butyl-3-hydroxy-2,3-dihydro-5-benzofuranyl)acetamide [9a] (2.50 g, 10.0 mmol), p-toluenesulfonic acid monohydrate (0.19 g, 1.0 mmol) and dichloromethane (30 mL) was stirred for 1 hour at room temperature and passed through short silica gel column. The column was washed with dichloromethane (300 mL). The solvent was evaporated under reduced pressure to give 2.11 g (91.3%) of N-(2-butyl-5-benzofuranyl)acetamide [10a] as off-white crystals with mp 71-73° C.

$^1$H NMR (CDCl$_3$): 8.07 (bs, 1H), 7.70 (d, J=2.0 Hz, 1H), 7.24 (d, J=8.0 Hz, 1H), 7.11 (dd, J=8.0 and 2.0 Hz, 1H), 6.24 (s, 1H), 2.70 (t, J=7.0 Hz, 2H), 2.10 (s, 3H), 1.67 (m, 2H), 1.41 (m, 2H), 0.92 (t, J=7.0 Hz, 3H).

Example 6

2-Butyl-5-benzofuranamine hydrochloride [12a]

Scheme 15

2-Butyl-5-benzofuranamine hydrochloride [12a]

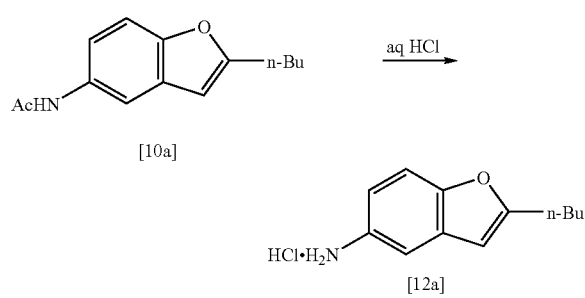

A mixture of N-(2-butyl-5-benzofuranyl)acetamide [10a] (1.16 g, 5.0 mmol) and 15% hydrochloric acid (10 mL) was stirred overnight under reflux conditions and 2 hours at 0-5° C. The precipitated crystals were filtered off, washed on the filter with cold water and ethyl acetate and dried under reduced pressure at 50° C. (water bath) to a constant weight to give 1.00 g (88.6%) of 2-butyl-5-benzofuranamine hydrochloride [12a] as off-white crystalls with mp 189-192° C. (with decomposition).

Example 7

Scheme 16

N-(2-Butyl-5-benzofuranyl)methanesulfonamide [14]

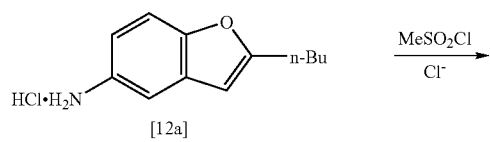

-continued

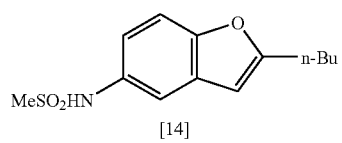
[14]

Methanesulfonyl chloride (0.92 g, 0.6 mL, 8.0 mmol) was added dropwise to a stirred boiling mixture of 2-butyl-5-benzofuranylamine hydrochloride [12a] (0.90 g, 4.0 mmol), tetramethylammonium chloride (0.11 g, 1.0 mmol) and toluene (10 mL) for 1 hour. The mixture was stirred under reflux conditions for 1 hour. Ethyl acetate (20 mL) and water (30 mL) were added to the cold mixture. The organic layer was separated and aqueous layer was extracted with ethyl acetate (2×20 mL). The combined organic layers were dried over sodium sulfate and evaporated under reduced pressure to give 1.01 g (94.0%) of N-(2-butyl-5-benzofuranyl)methanesulfonamide [14] with mp 104.9-105.9° C.

$^1$H NMR (CDCl$_3$): 7.40 (d, J=2.2 Hz, 1H), 7.35 (d, J=8.6 Hz, 1H), 7.05 (dd, J=8.6 and 2.2 Hz, 1H), 6.63 (s, 1H), 6.34 (s, 1H), 2.95 (s, 3H), 2.74 (t, J=7.2 Hz, 2H), 1.71 (m, 2H), 1.39 (m, 2H), 0.93 (t, J=7.2 Hz, 3H).

Example 8

Scheme 17

N-(2-Butyl-5-benzofuranyl)methanesulfonamide [14]

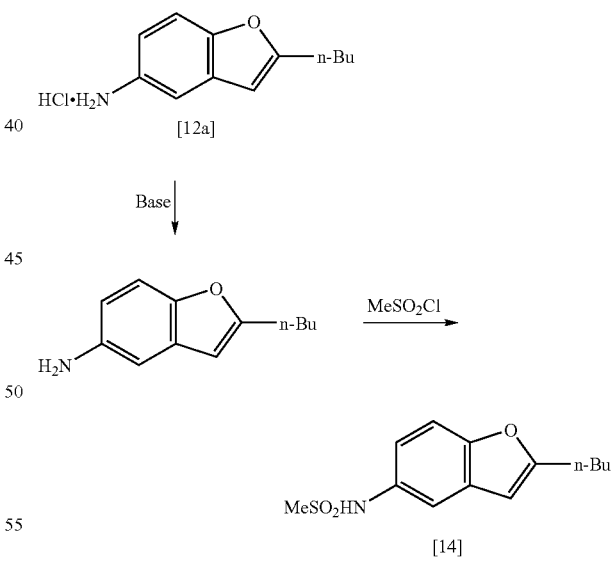

A mixture of 2-butyl-5-benzofuranamine hydrochloride [12a] (3.16 g, 14.0 mmol) and toluene (30 mL) and a solution of sodium hydroxide (0.6 g, 15.0 mmol) in water (30 mL) were stirred for 0.5 hour at room temperature. The organic layer was separated and the aqueous layer was extracted with toluene (2×30 mL). The combined organic layers were dried over sodium sulfate, filtered and concentrated to the volume of 30 mL.

A solution of methanesulfonyl chloride (1.98 g, 17.2 mmol, 1.3 equiv.) in toluene (10 mL) was added dropwise over period of 1 hour to the stirred boiling mixture. The mixture was stirred for 2 hour under reflux conditions. Hexane (40 mL) was added to the mixture at room temperature. The obtained suspension was stirred for 0.5 hour at 0-5° C. (ice/water bath). The precipitated crystals were filtered and dissolved in dichloromethane (30 mL). The solution was filtered through short silica gel column (5 g). The column was washed with dichloromethane and combined filtrates were evaporated under reduced pressure at 50-60° C. (water bath) to give 3.41 g (91.0%) of N-(2-butyl-5-benzofuranyl)methanesulfonamide [14] (one spot on TLC).

Example 9

Scheme 18

Dronedarone [1]

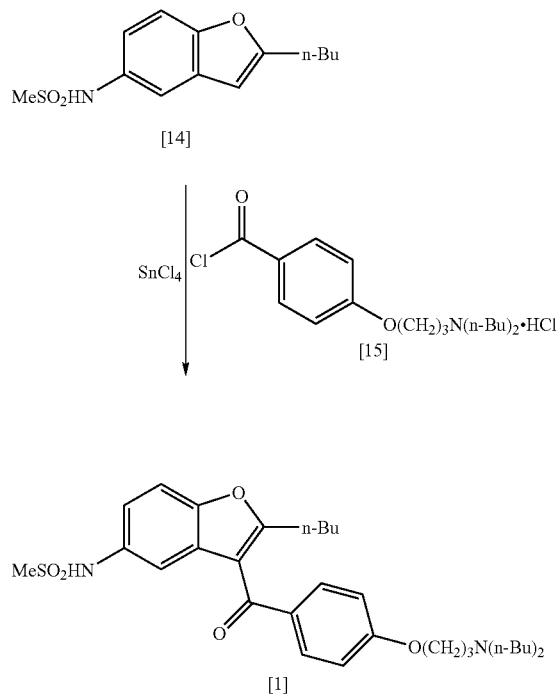

Tin (IV) chloride (2.7 mL, 23.0 mmol) was added dropwise to a stirred solution of N-(2-butyl-5-benzofuranyl)methanesulfonamide [14] (2.50 g, 9.4 mmol) and 4-(3-dibutylaminopropoxy)benzoyl chloride hydrochloride [15] (3.62 g, 10.0 mmol) in dichloromethane (20 mL) at 0-5° C. The mixture was stirred for 30 min at the same temperature and for 2 hours at room temperature. Water (50 mL) was added dropwise to the stirred mixture at 0-5° C. The mixture was extracted with dichloromethane (3×30 mL). The combined organic layers were washed with saturated sodium bicarbonate aqueous solution, dried over sodium sulfate and evaporated. 3.45 g (65.9%) of dronedarone [1] was obtained after purification of the residue by column chromatography on silica gel (ethyl acetate/hexane 1:3 v/v).

$^1$H NMR (CDCl$_3$): 7.77 (d, J=8.5 Hz, 2H), 7.27 (m, 3H), 6.91 (d, J=8.5 Hz, 2H), 5.52 (bs, 1H), 4.05 (t, J=6.0 Hz, 2H), 2.87 (s, 3H), 2.79 (t, J=7.0 Hz, 2H), 2.57 (t, J=7.0 Hz, 2H), 2.39 (t, J=7.0 Hz, 4H), 1.90 (m, 2H), 1.68 (m, 2H), 1.33 (m, 10H), 0.82 (m, 9H).

Example 10

Scheme 19

Dronedarone hydrchloride [1a]

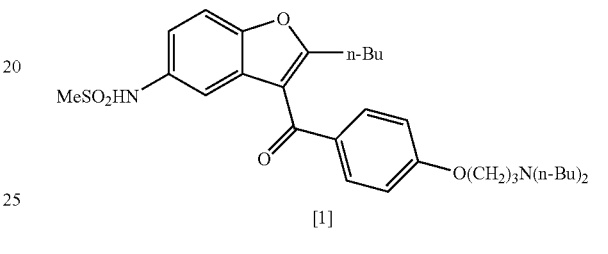

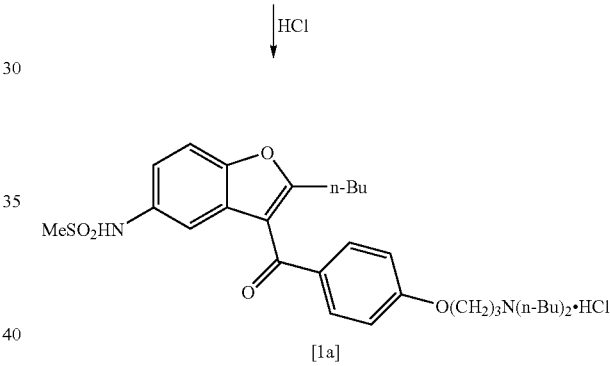

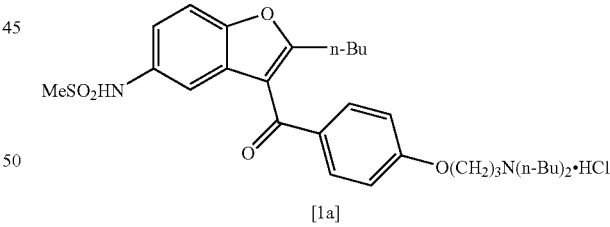

Hydrogen chloride, 10% solution in ethyl acetate (2.5 mL, 7.00 mmol), was added dropwise to a stirred solution of dronedarone (3.40 g, 6.00 mmol) in ethyl acetate (30 mL) at 0-5° C. (ice/water bath). The mixture was stirred for 1 hour at the same temperature and evaporated under reduced pressure at 50-60° C. (water bath) to give dronedarone hydrochloride [1a].

$^1$H NMR (CDCl$_3$): 11.56 (bs, 1H), 8.18 (s, 1H), 7.72 (d, J=8.5 Hz, 2H), 7.27 (m, 3H), 6.87 (d, J=8.5 Hz, 2H), 4.15 (m, 2H), 3.23 (m, 2H), 3.03 (m, 5H), 2.86 (s, 3H), 2.37 (m, 2H), 2.00 (m, 1H), 1.74 (m, 6H), 1.33 (m, 6H), 0.88 (m, 9H).

Example 11

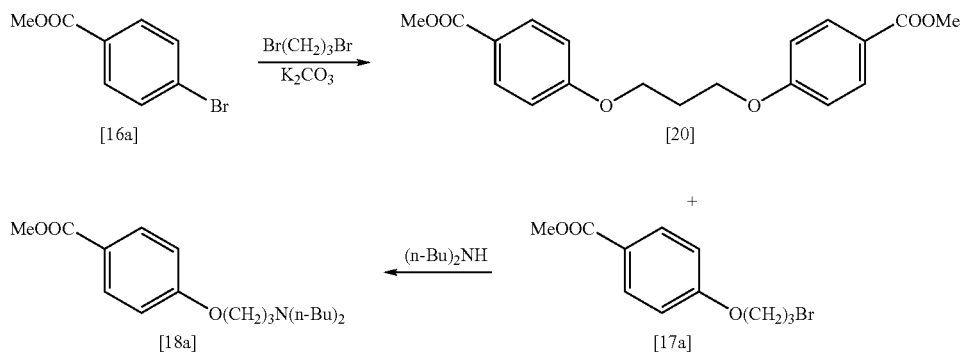

A mixture of methyl 4-hydroxybenzoate [16a] g, 150 mmol), potassium carbonate (41.49 g, 300 mmol), 1,3-dibromopropane (170.00 g, 842 mmol) and methyl ethyl ketone (MEK) (200 mL) were stirred under reflux conditions for 6 hours. The cold mixture was filtered off and solids on the filter was washed with MEK (100 mL). The combined filtrates were evaporated under reduced pressure at 90° C. to give the mixture of methyl 4-(3-bromopropoxy)benzoate and dimethyl 4,4'-[1,3-propanediylbis(oxy)]bisbenzoate (41.00 g). Analytical samples of methyl 4-(3-bromopropoxy)benzoate [17a] methyl 4,4'-[1,3-propanediylbis(oxy)] bisbenzoate [20] isolated from the mixture by column chromatography on silica gel. Methyl 4-(3-bromopropoxy)benzoate [17a] $^1$H NMR (CDCl$_3$): 7.95 (d, J=8.8 Hz, 2H), 6.88 (d, J=8.8 Hz, 2H), 4.11 (t, J=7.0 Hz, 2H), 3.84 (s, 3H), 3.56 (t, J=7.0 Hz, 2H), 2.29 (m, 2H). Dimethyl 4,4'-[1,3-propanediylbis(oxy)]bisbenzoate [20] $^1$H NMR (CDCl$_3$): 7.96 (d, J=8.8 Hz, 4H), 6.90 (d, J=8.8 Hz, 4H), 4.20 (t, J=7.0 Hz, 4H), 3.86 (s, 6H), 2.28 (m, 2H).

A solution of the mixture of methyl 4-(3-bromopropoxy)benzoate [17a] methyl 4,4'-[1,3-propanediylbis(oxy)]bisbenzoate [20] previous step (19.12 g) and dibutylamine (27.14 g, 35.7 mL, 210 mmol) in toluene (50.0 mL) was stirred under reflux conditions for 3 hours, cooled and extracted with 15% hydrochloric acid (3×40 mL). The combined aqueous layers were washed with of toluene (50 mL), basified to pH 8.5 with sodium bicarbonate and extracted with toluene (3×30 mL). The combined organic layers were dried over sodium sulfate, filtered and evaporated under reduced pressure at 60° C. (water bath). The residue was dissolved in hexane and passed through thin layer of silica gel. The solvent was evaporated under reduced pressure at 50-60° C. (water bath) to give 14.71 g (61.1% yield from 2 steps) of methyl 4-(3-dibutylaminopropoxy)benzoate [18a] as an oil.

$^1$H NMR (CDCl$_3$): 7.95 (d, J=8.6 Hz, 2H), 6.88 (d, J=8.6 Hz, 2H), 4.04 (t, J=7.0 Hz, 2H), 3.85 (s, 3H), 2.55 (t, J=7.0 Hz, 2H), 2.38 (t, J=7.0 Hz, 4H), 1.86 (m, 2H), 1.34 (m, 8H), 0.86 (t, J=7.0 Hz, 6H).

Example 12

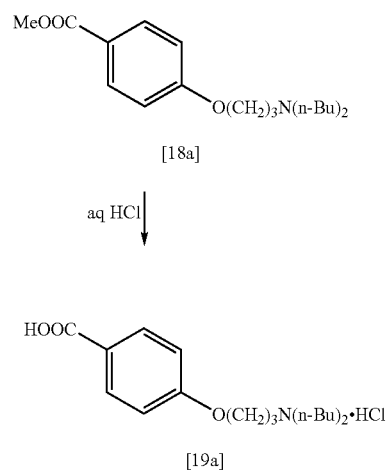

A mixture of methyl 4-(3-dibutylaminopropoxy)benzoate [18a] (7.65 g, 23.8 mmol) and 32% hydrochloric acid (30 mL) was stirred for 5 hours under reflux conditions and for one hour at 0-5° C. (ice/water bath). The suspension was filtered. The precipitated crystals were washed on the filter with water and hexane and dried under reduced pressure at 50-60° C. (water bath) to give 6.90 g (85.7%) of 4-(3-dibutylaminopropoxy)benzoic acid hydrochloride [19a] as white crystals with mp 157-159° C.

$^1$H NMR (CDCl$_3$): 11.75 (bs, 1H), 7.93 (d, J=8.7 Hz, 2H), 6.80 (d, J=8.7 Hz, 2H), 4.09 (m, 2H), 3.24 (m, 2H), 3.02 (m, 4H), 2.37 (m, 2H), 1.78 (m, 4H), 1.36 (m, 4H), 0.93 (t, J=7.2 Hz, 6H).

Example 13

Scheme 22
4-(3-Dibutylaminopropoxy)benzoic chlroide hydrochloride [15]

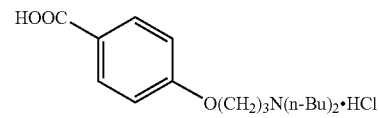

[19a]

↓ SOCl₂

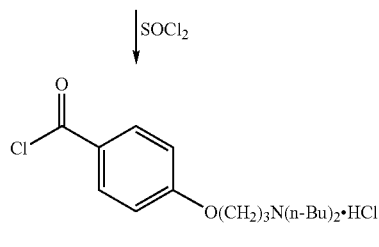

[15]

A mixture of 4-(3-dibutylaminopropoxy)benzoic acid hydrochloride [19a] (3.44 g, 10.0 mmol), thionyl chloride (5.87 g, 3.6 mL, 49.4 mmol) and dichloromethane (10 mL) was stirred under reflux conditions for 1 hour and evaporated under reduced pressure at 60-70° C. (water bath) to give 3.62 g (100% yield) of 4-(3-dibutylaminopropoxy)benzoyl chloride hydrochloride [15].

What is claimed is:

1. A process for preparing dronedarone [1]

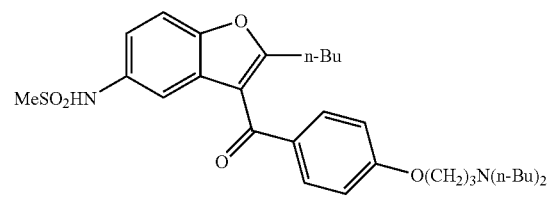

or a pharmaceutically acceptable salt thereof, which process comprises the steps of:

(a) reacting a compound of formula [3] with 2-bromohexanoyl chloride or bromide in the presence of aluminum chloride or bromide to obtain a compound of formula [6]:

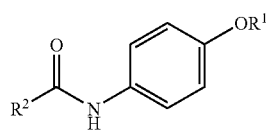

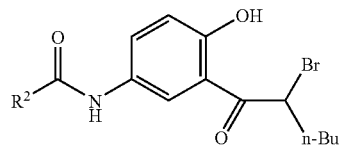

wherein $R^1$ is methyl or ethyl; and $R^2$ is selected from the group consisting of alkyl, aryl, aralkyl, alkoxy, aryloxy and aralkoxy;

(b) converting the compound [6] obtained in step (a) above into the compound of formula [9]

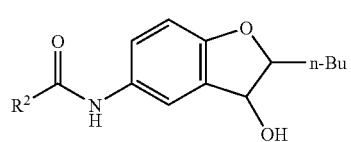

(c) dehydrating and N-deprotecting the compound of formula [9] obtained in step (b) above in an aqueous solution of $HX^4$, wherein $HX^4$ is selected from the group consisting of hydrogen chloride, hydrogen bromide, sulfuric acid, methanesulfonic acid and p-toluenesulfonic acid, to obtain the solid acid addition salt of 2-butyl-5-benzofuranamine [12]

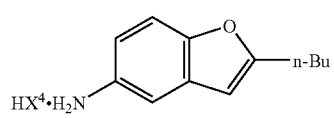

(d) optionally, preparing 2-butyl-5-benzofuranamine free base from the acid addition salt of 2-butyl-5-benzofuranamine [12] obtained in step (c) above;

(e) reacting the 2-butyl-5-benzofuranamine free base obtained in step (d) above or the acid addition salt of 2-butyl-5-benzofuranamine [12] obtained in step (c) with an agent selected from the group consisting of methanesulfonic anhydride and methanesulfonyl chloride or fluoride to obtain N- (2-butyl-5-benzofuranyl)methanesulfonamide [14]

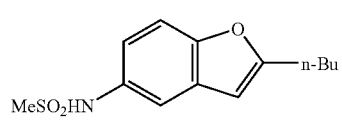

(f) Friedel-Crafts acylating of N (2-butyl-5-benzofuranyl)methanesulfonamide [14] obtained in step (e) above with 4- (3-dibutylaminopropoxy)benzoyl chloride hydrochloride [15]

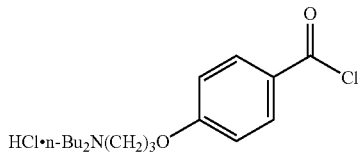

to obtain dronedarone [1] or a pharmaceutically acceptable salt thereof.

2. The process of claim 1 wherein compound 6 is converted into the compound of formula [9] in step (b) without isolating the intermediate compounds [7] and [8]:

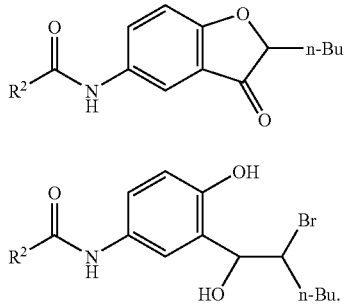

3. The process of claim 1 wherein compound [12] is obtained in step (c) without isolating the intermediate compounds [10] and [11]:

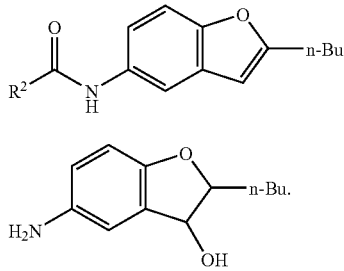

4. The process of claim 1, wherein $R^2$ is a methyl group.

5. The process of claim 1, wherein $HX^4$ is hydrogen chloride.

6. A compound of formula [6]:

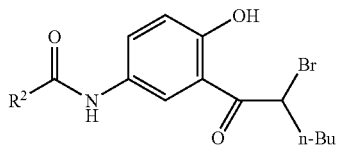

wherein $R^2$ is selected from the group consisting of alkyl, aryl, aralkyl, alkoxy, aryloxy and aralkoxy.

7. A compound of formula [7]:

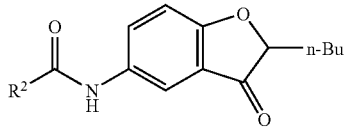

wherein $R^2$ is selected from the group consisting of alkyl, aryl, aralkyl, alkoxy, aryloxy and aralkoxy.

8. A compound of formula [9]:

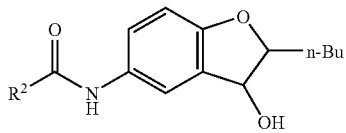

wherein $R^2$ is selected from the group consisting of alkyl, aryl, aralkyl, alkoxy, aryloxy and aralkoxy.

9. A compound of formula [10]:

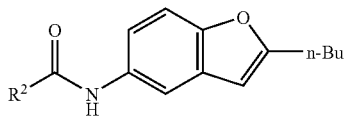

wherein $R^2$ is selected from the group consisting of alkyl, aryl, aralkyl, alkoxy, aryloxy and aralkoxy.

10. The compound of claim 6 wherein $R^2$ is methyl.
11. The compound of claim 7 wherein $R^2$ is methyl.
12. The compound of claim 8 wherein $R^2$ is methyl.
13. The compound of claim 9 wherein $R^2$ is methyl.
14. A process according to claim 1 for the preparation of dronedarone [1] or apharmaceutically acceptable salt thereof:

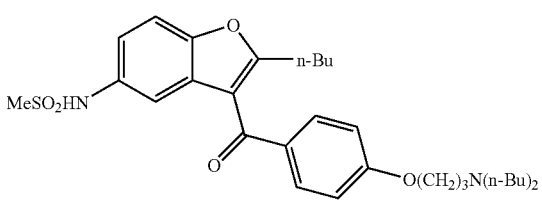

such process comprising the steps of:

N-acetylating of p-anisidine or p-phenetidine with acetic anhydride, reacting of the obtained N-(4-alkoxyphenyl) acetamide with 2-bromohexanoyl chloride or bromide in the presence of aluminum chloride or bromide to obtain N-[3-(2-bromohexanoyl)-4-hydroxyphenyl] acetamide [6a], converting the compound [6] into 2-butyl-5-benzofuranamine hydrochloride [12a] and subsequently converting [12a] into [1] or a pharmaceutically acceptable salt thereof.

15. A compound of formula [6]:

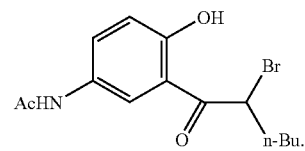

[6a]

* * * * *